United States Patent
Lee

(10) Patent No.: US 9,050,040 B2
(45) Date of Patent: Jun. 9, 2015

(54) INTRAORAL RADIATION TYPE X-RAY PHOTOGRAPHING APPARATUS AND METHOD THEREOF

(75) Inventor: Rena Lee, Seoul (KR)

(73) Assignee: EWHA UNIVERSITY-INDUSTRY COLLABORATION FOUNDATION, Seoul (KR)

(*) Notice: Subject to any disclaimer, the term of this patent is extended or adjusted under 35 U.S.C. 154(b) by 293 days.

(21) Appl. No.: 13/635,129

(22) PCT Filed: Mar. 23, 2011

(86) PCT No.: PCT/KR2011/001972
§ 371 (c)(1),
(2), (4) Date: Sep. 14, 2012

(87) PCT Pub. No.: WO2011/118973
PCT Pub. Date: Sep. 29, 2011

(65) Prior Publication Data
US 2013/0010923 A1    Jan. 10, 2013

(30) Foreign Application Priority Data
Mar. 24, 2010 (KR) .................. 10-2010-0026174

(51) Int. Cl.
*A61B 6/14* (2006.01)
*A61B 6/06* (2006.01)
*A61B 6/00* (2006.01)
*H01J 35/32* (2006.01)

(52) U.S. Cl.
CPC . *A61B 6/145* (2013.01); *A61B 6/06* (2013.01); *A61B 6/4007* (2013.01); *A61B 6/4057* (2013.01); *A61B 6/4208* (2013.01); *A61B 6/4233* (2013.01); *H01J 35/32* (2013.01); *H01J 2235/0233* (2013.01); *H01J 2235/166* (2013.01); *H01J 2235/18* (2013.01)

(58) Field of Classification Search
CPC ........ A61B 6/14; A61B 6/145; A61N 5/1014; H01J 35/065

USPC ............................................ 378/38, 121, 122
See application file for complete search history.

(56) References Cited

U.S. PATENT DOCUMENTS

| 7,771,117 B2 | 8/2010 | Kim et al. | |
| 2009/0080614 A1* | 3/2009 | Eaton et al. | 378/122 |
| 2009/0310742 A1* | 12/2009 | Kim et al. | 378/38 |
| 2010/0303204 A1* | 12/2010 | Erhardt et al. | 378/62 |

FOREIGN PATENT DOCUMENTS

| JP | 05-068679 A | 3/1993 |
| JP | 06-254087 A | 9/1994 |
| KR | 10-2009-0129942 A | 12/2009 |

OTHER PUBLICATIONS

International Search Report issued in corresponding application, PCT/KR2011/001972, dated Nov. 30, 2011.

* cited by examiner

*Primary Examiner* — Michael Maskell
(74) *Attorney, Agent, or Firm* — Lee & Morse, P.C.

(57) ABSTRACT

The present invention provides an X-ray imaging system for capturing an X-ray image of teeth and a jawbone, including a tubular X-ray generating unit placed in an oral cavity, and a movable X-ray detection unit placed in the oral cavity outer side region corresponding to the X-ray generating unit and corresponding to a face or an X-ray detection unit having a curved surface shape similar to the face.

The present invention having the configuration may obtain a teeth X-ray image with a large surface area while minimizing the dose of X-ray exposed to a patient by placing an X-ray generating device in the oral cavity and disposing a movable sensor or a sensor with a large surface area on the outer side of the oral cavity to obtain an X-ray image, reduce excessive X-ray exposure and foreign body sensation in the oral cavity, which a panoramic mode X-ray generating device or an oral sensor-type X-ray generating device in the related art has, to enhance the safety and convenience of the patient, and obtain a clear image with a large surface area, which helps a medical staff in making an exact judgment, with the least number of shootings.

20 Claims, 3 Drawing Sheets

US 9,050,040 B2

INTRAORAL RADIATION TYPE X-RAY PHOTOGRAPHING APPARATUS AND METHOD THEREOF

TECHNICAL FIELD

The present invention relates to an X-ray imaging system, and particularly, to an X-ray imaging system which may rapidly and conveniently obtain images of teeth and a jawbone, which are used in dental treatment.

BACKGROUND ART

In general, medical experts such as dentists make diagnostic decisions through X-ray imaging using an X-ray imaging system for detecting a disease (for example, detection of detailed tooth condition such as small cavities, extended periodontal ligament space, or the like) and accordingly take appropriate measures.

In order to X-ray images of teeth and a jawbone by using an X-ray imaging method in the related art, there is used a method for continuously photographing the teeth and the jawbone over and over again, including: inserting a sensor or film into the oral cavity, positioning an intraoral X-ray unit for X-ray imaging outside the patient, irradiating X-ray, and changing the position of the sensor again.

Another method includes a method for making X-ray imaging by using an apparatus for panoramic imaging, including: placing an X-ray generator and an X-ray detector outside such that the head of a patient is placed therebetween and making X-ray imaging with a certain frame while rotating the X-ray generator and the X-ray detector.

In the former method, a hard square-shaped sensor is inserted into the oral cavity of a patient, and thus the patient feel a foreign object in the oral cavity. Further, it is impossible to exactly maintain the position of the sensor during imaging and the sensor is not manufactured to fit the oral structure of each patient, and thus a case where an actually desired image may not be obtained with one X-ray exposure occurs and a process of again positioning the sensor and capturing an image is repeated, thereby making the patient feel uncomfortable and resulting in irradiation of unnecessary radiation.

The latter panoramic imaging apparatus is advantageous in that the continuous arrangement of teeth and the upper jaw or the lower jaw may be confirmed with an image when images are continuously captured and subjected to an image treatment of a computer, but is disadvantageous in that expensive X-ray equipment rotating about an axis is required and much space for equipment is required due to a large radius of the gyration. In addition, images are obtained after X-ray imaging several tens of times, and thus the method is disadvantageous in that the dose of X-ray radiation exposed to a patient is increased.

DISCLOSURE

Technical Problem

Thus, the present invention is a technical idea to solve the above-described problems and provides an intraoral radiation type X-ray imaging system which does not give a foreign body sensation to a patient, easily maintain the exact position of a sensor during photographing, may obtain a desired image with an one-time X-ray exposure to reduce the inconvenience of the patient in the X-ray imaging, and may perform photographing without irradiation of unnecessary radiation.

Furthermore, the present invention provides an intraoral radiation type X-ray imaging system which does not need expensive X-ray equipment rotating about an axis, may compactly decrease the space for equipment, and may decrease the dose of X-ray radiation exposed to a patient by reducing the number of X-ray irradiation times.

Technical Solution

The intraoral radiation type X-ray imaging system according to the present invention for capturing an X-ray image of teeth or a jawbone includes: a tubular X-ray generating unit placed in the oral cavity; an X-ray detection unit with a large surface area corresponding to the tubular X-ray generating unit and placed in a region on the outer side of the oral cavity, and an X-ray generating unit support which allows the position of the X-ray generating unit in the oral cavity to be exactly placed such that an affected part of the patient is appropriately imaged with a minimal dose of radiation.

The X-ray generating unit preferably includes an X-ray tube that radially generates X-rays, a collimator provided with an insertion space into which the X-ray tube is inserted, and an X-ray generator including at least one collimator hole provided in the collimator in order to radiate X-rays emitted from the X-ray tube to a necessary region.

As the X-ray generating unit, a field electron emission-based X-ray tube or thermoelectronic emission-based X-ray tube of a nano-composite material may be used. The X-ray generating tube may be a diameter of 0.5 to 10 mm and a length of 0.5 to 4 cm, and has a tube current of 0.1 to 1 mA and a tube voltage of 50 to 100 kVp. The X-ray tube includes an X-ray generating source for generating electron-excited X-ray and an electron emitting source for emitting electrons, and the distance from the electron emitting source to the X-ray generating source may be 3 cm or less. When the distance exceeds 3 cm, it is difficult to place the X-ray generating unit in the oral cavity, and electrons does not exactly reach the X-ray generating source, and thus a sufficient dose of X-ray radiation is not radiated, thereby deteriorating the quality of X-ray images obtained. The X-ray generated from the X-ray generating unit has a characteristic of being radiated at an angle of 360° based on the center. In order to achieve the miniaturization of the X-ray generating unit placed in the oral cavity, the X-ray generating source, the electron emitting source and a power connection unit may be disposed on the same straight line axis, and when the elements are disposed on the same straight line, effects of a high voltage power line applied from the outside on the movement of electrons emitted from the electron emitting source are minimally exerted, thereby improving the stability of operating the X-ray generating device.

The X-ray generating unit support includes a power supply line for applying high voltage to the electron emitting source in the X-ray generating unit and serves to fix the position of the X-ray generating unit. The X-ray generating unit support is a multi-joint bending support or may be supported by using a flexible tube, a tube having a spiral pattern, or the like, and freely places the X-ray generating unit in the vicinity of teeth or a jawbone in the oral cavity to be obtained, or placed at the center of the oral cavity in order to obtain an image of all the teeth.

The X-ray detection unit may use any one of a CMOS, a CCD, a non-pixel-based sensor, an amorphous silicon sensor, and a GEM detector in order to obtain a digital image, and it is possible to obtain an image even though an X-ray film in the related art may be used. In particular, in order to obtain an image of a plurality of teeth, an X-ray detection unit having various sizes and shapes may be used. Typically, an intraoral detector is configured by a sensor having a size of 1.5×1 cm. The reason is that the detector is placed in the oral cavity and thus it is difficult to select a sensor having a larger size. However, the present invention has a structure in which the X-ray generating source is placed in the oral cavity, and thus it is fairly free to select the size of a detector. It is also possible to adopt a large-size detection sensor capable of obtaining information on as many teeth as possible at one time shooting, and it is also possible to use an X-ray detection unit which corresponds to an X-ray generator whose position is internally fixed and captures images while moving outside. In order to perform the panoramic photographing using the present invention, it is most preferred to constitute and use a single detector including a length or longer covering all of the upper jaw and lower jaw of a patient in a transverse direction and a length or longer covering the dental root of the upper jaw and lower jaw of a patient in a longitudinal direction. However, in this case, the price of the detector is increased and due to different oral cavity structures and sizes for everybody, it is necessary to possess a plurality of detecting devices or the detector needs to have a modifiable shape. Another method is to use a method for capturing an X-ray image, including: performing X-ray emission several times while the position of an X-ray detector in the oral cavity is temporarily fixed and synchronizing with the X-ray emission timing of the X-ray generating unit while the external X-ray detection unit moves along the face of the patient outside the oral cavity. These methods are advantageous in that the costs are reduced due to equipment being a simpler structure than panoramic equipment in the related art and less space is required. Further, according to the size selection of the X-ray detection unit, the methods are advantageous in that the X-ray image of all the teeth may be obtained with continuous photographing repeated at least three times. In addition, when a rotation type collimator of the X-ray generating unit is used, the methods are advantageous in that the X-ray exposure dose of a patient is minimized by selecting only a part appropriate for the position of the external X-ray detection unit as X-ray radiation direction to radiate X-ray.

Furthermore, a method for capturing an X-ray image of oral cavity or jawbone through an intraoral radiation type X-ray imaging system including an X-ray generating unit, an X-ray detection unit, and an X-ray generating unit support according to the present invention, includes: transferring the X-ray generating unit and the support to dispose the X-ray generating unit to a photographing region of teeth or the jawbone of the patient; disposing the X-ray detection unit on the outer side of the oral cavity, which corresponds to the photographing region which is equivalent to the X-ray generating unit; adjusting the positions such that the X-ray generating unit and the X-ray detection unit face each other; and applying a voltage for generating the X-ray to the X-ray generating unit to obtain an X-ray image. Simple equipment may be used to obtain a panoramic image of teeth by repeatedly performing the above-described method.

Advantageous Effects

As described above, the present invention minimizes the inconvenience for a patient and a medical staff by placing a small tubular X-ray generating device in the oral cavity and disposing an X-ray detection unit with a large surface area on the outer side of the oral cavity to obtain an X-ray image, thereby obtaining an X-ray image of the entire oral cavity with a minimal photographing.

That is, the present invention may place a tubular X-ray generating device in the oral cavity and connect an external high voltage power source to the device to generate an X-ray. The X-ray generated may be widely radiated at a certain angle or more to be radiated and pass through a tooth or a jawbone connected to the tooth to display an image on the X-ray detection unit disposed on the outer side of the oral cavity.

As described above, the present invention may provide an X-ray imaging system, which is small-sized compared to the intraoral X-ray detector in the related art and enables a plurality of teeth or the jawbone to be exactly photographed by placing a tubular X-ray generating device capable of emitting radiation at 360° in the oral cavity, thereby reducing unnecessary exposure of a patient to radiation.

Furthermore, the present invention may use an X-ray detector with a large surface area to obtain a plurality of exact X-ray images of teeth at one time shooting, and an X-ray imaging of all the teeth in the oral cavity may be obtained by irradiating radiation once according to the selection of an X-ray detector.

BEST MODE

Figure 1:
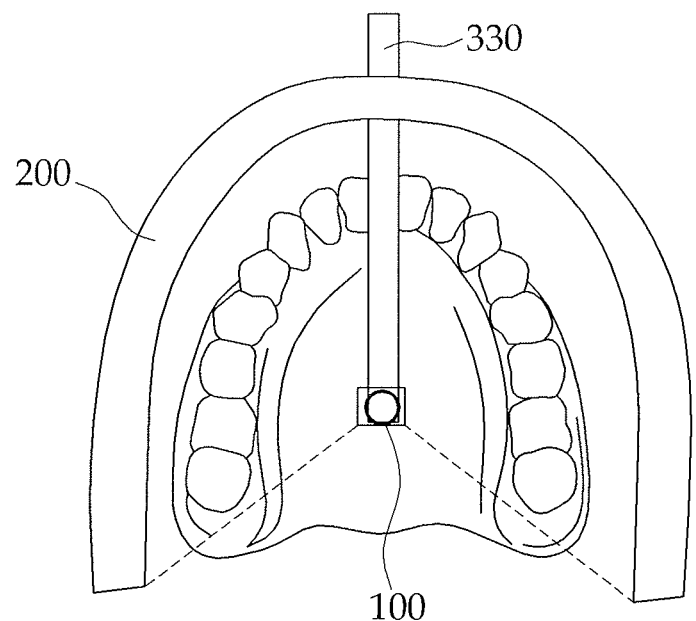
FIG. 1 is an operation conceptual view of an X-ray imaging system according to an exemplary embodiment of the present invention.

Hereinafter, exemplary embodiments of the present invention will be described in more detail with reference to the accompanying drawings. However, the present invention is not limited to the exemplary embodiments to be disclosed below, but various forms different from each other may be implemented. However, the exemplary embodiments are provided to make the disclosure of the present invention complete and to completely inform those skilled in the art of the scope of the invention. In the drawings, like reference numerals indicate like elements.

Figure 2:
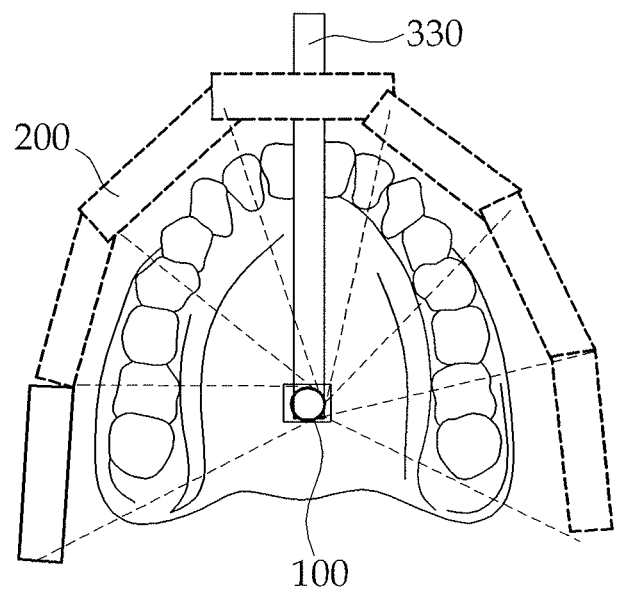
FIG. 2 is an operation conceptual view of an X-ray imaging system according to another exemplary embodiment of the present invention.
Figure 3:
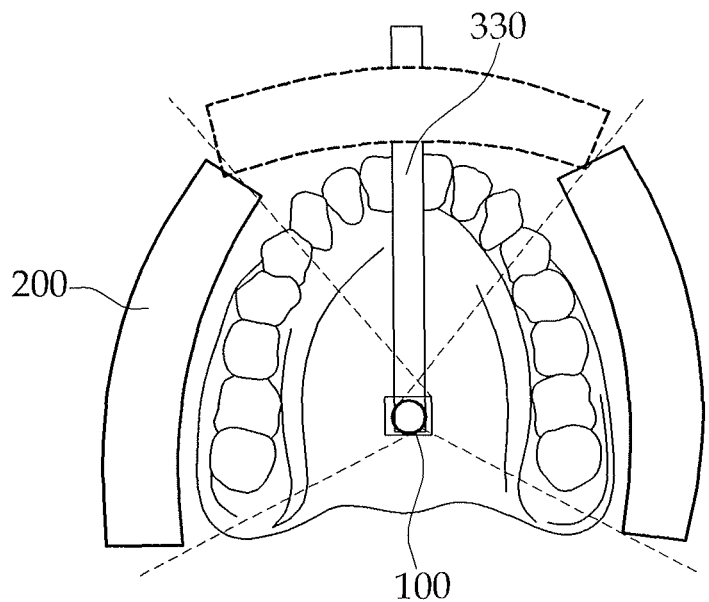
FIG. 3 is an operation conceptual view of an X-ray imaging system according to yet another exemplary embodiment of the present invention.
Figure 4:
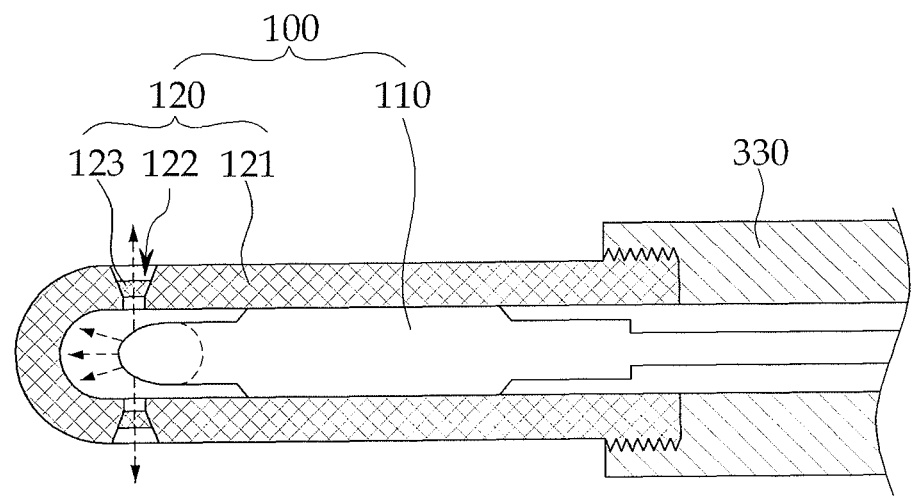
FIG. 4 is a cross-sectional conceptual view of an X-ray generating unit support according to an exemplary embodiment of the present invention.
Figure 5:
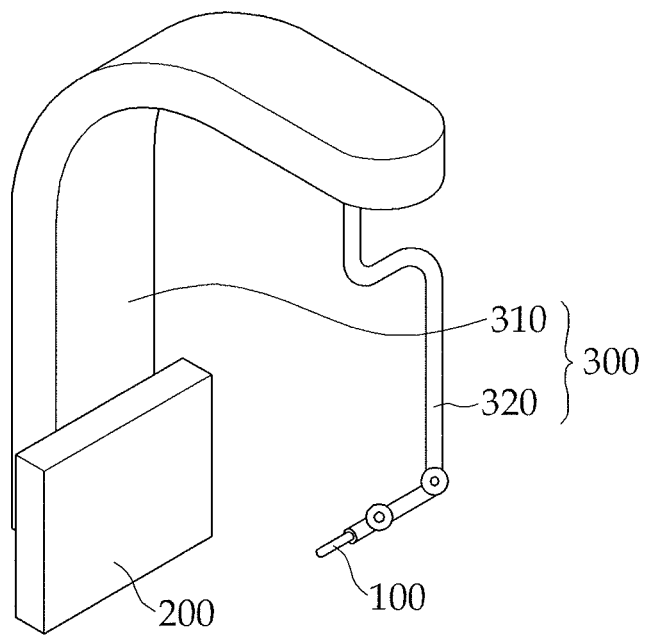
FIG. 5 is a perspective view of an intraoral X-ray imaging system according to an exemplary embodiment of the present invention.
Figure 6:
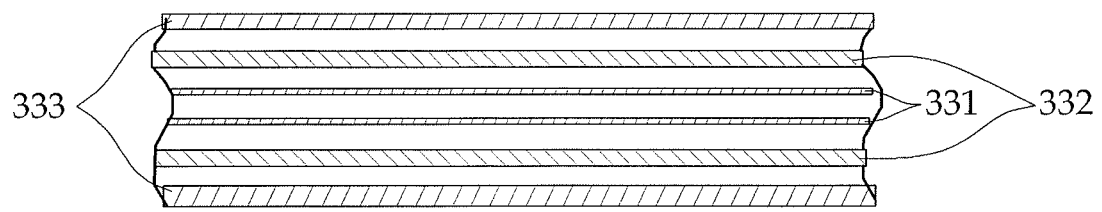
FIG. 6 is a longitudinal cross-sectional view of a power supply connection line according to an exemplary embodiment of the present invention.

FIG. 1 is an operation conceptual view of an X-ray imaging system according to an exemplary embodiment of the present invention. FIG. 2 is an operation conceptual view of an X-ray imaging system according to another exemplary embodiment of the present invention. FIG. 3 is an operation conceptual view of an X-ray imaging system according to yet another exemplary embodiment of the present invention. FIG. 4 is a cross-sectional conceptual view of an X-ray generating unit according to an exemplary embodiment of the present invention FIG. 5 is a view of an X-ray imaging system according to an exemplary embodiment of the present invention. FIG. 6 is a cross-sectional conceptual view of an X-ray generating unit support according to an exemplary embodiment of the present invention.

Referring to FIGS. 1 to 6, the X-ray imaging system according to the present invention relates to an X-ray imaging system including: an X-ray generating unit 100 placed in an oral cavity and configured to generate radiation, an X-ray detection unit placed on the outer side of the oral cavity and configured to obtain an image of both the entire teeth and the jawbone or an X-ray detection unit 200 configured to obtain a continuous image of a plurality of teeth and the corresponding jawbone by using X-ray images obtained through continuous moving, and an X-ray generating unit support 330 configured to place the X-ray generating unit 100 at an exact position in the oral cavity.

As illustrated in FIG. 1, the X-ray generating unit 100 is a small tubular unit and placed in the center of the oral cavity, and the structure and size of the X-ray detection unit 200 outside the oral cavity is freely selected because an X-ray emitting source is placed in the oral cavity. As an exemplary embodiment of the present invention, the X-ray detection unit 200, which adopts an X-ray detection sensor having flexibility, is designed to have a curved surface to fit the facial structure of a patient, is typically designed to have a length of 22 cm or more, and may be manufactured to have a height of 10 cm or more, which may cover both the upper jaw and lower jaw. However, when the upper jaw or lower jaw is separately measured, if necessary, it is also possible to design the detection unit into a smaller size.

The X-ray generating device is tubular, an electron generating source and an X-ray generating source are disposed on the same straight line axis from a connection unit of a high voltage power source, and the X-ray generated from the X-ray generating source is radiated out from an angle at 360°. Accordingly, it is easy to determine a necessary radiation direction through a collimator, and when the X-ray is set to be radiated out at 180° to 360° by the collimator, an X-ray image of the upper jaw or the lower jaw or the entire upper and lower jaws may be obtained at one time shooting. The X-ray generating unit has a structure that the X-ray is radiated out at 360° from the internal X-ray generating source, but adopts a collimator which allows the X-ray to be emitted only at a certain angle for a part that has nothing to do with the X-ray imaging in order to reduce the radiation exposure dose of a patient. The collimator also serves to block the X-ray from being radiated to a region (brain and visual nerve part) other than the imaging region. Accordingly, the present invention is advantageous in that a medical staff may obtain an exact image with the least number of shootings and the exposure of X-ray to the patient may be minimized by minimizing unnecessary X-ray shooting. In the drawing, as the X-ray generating unit support 330, a linear support type device capable of controlling an angle is used, but a tubular form having a spiral pattern or a support made of a material having elasticity may be used. The present invention is advantageous in that the position of the X-ray generating unit 100 may be freely regulated in the oral cavity of the patient according to an image to be obtained by using the X-ray generating unit support 330 which has joints or is flexible or elastic. It is possible to safely radiate a patient and a medical staff can retrieve exact and rapid information by photographing the entire region of teeth with one time irradiation of radiation as in the present embodiment to greatly reduce the inconvenience caused by using an intraoral sensor method in the related art and the excessive radiation exposure resulting from panoramic equipment for photographing the oral cavity through external rotation equipment.

FIG. 2 illustrates a system including panoramic photographing equipment and general equipment for treatment of the oral cavity according to yet another exemplary embodiment of the present invention. In the present exemplary embodiment, the X-ray detection unit 200 is rotatably configured for each predetermined section outside the oral cavity. That is, the X-ray detection unit 200 may be connected to a sensor rotating arm which is configured to rotate. The X-ray detection unit 200 uses a method of measuring a dose of radiation when the radiation is emitted from the X-ray generator once, moving into the next position, and then measuring the dose of radiation emitted during the generation of X-ray again at the position rotated again. At this time, the X-ray generating unit 100 also may repeatedly emit X-ray to the entire region of teeth, and yet another method may include a method of rotating a rotation type collimator in synchronization with the movement of the X-ray detection unit by adopting the collimator and automatically adjusting the position. When a separable or rotatable collimator is used, it is possible to use the collimator to minutely control an X-ray to be radiated in a desired direction without changing the direction of the X-ray generating unit 100 per se, but there is a disadvantage in that a rotation device is provided in the X-ray generating unit, and thus the X-ray generating unit becomes complicated and large. Even when a fixed type collimator is used, it is also possible to change the X-ray emission direction from the outside by adding a rotation device to the X-ray generating unit support. The latter case is advantageous in that the dose of radiation exposed to a patient is small, but the X-ray generating source enables the X-ray to be continuously radiated several tens of times per second, and thus it is preferred that photographing is completed in a short time because blurring of images caused by the movement of the patient may be prevented. When the X-ray generating unit is placed in the central portion of a virtual rotation axis of the rotating X-ray detection unit, the most preferred image may be obtained. However, the moving trajectory of the rotation axis is not always circular, and it is also possible to have an elliptical trajectory which is the most similar to the shape of the oral cavity. In addition, the images obtained are processed to be reconfigured as one image through a computer device.

FIG. 3 illustrates a method of rotating the X-ray detection unit 200 having an X-ray detection sensor with a large surface area having a curved surface as a hybrid shape of the above exemplary embodiments to obtain a panoramic image. The present exemplary embodiment includes an X-ray detection unit 200 having a curvature with a large surface area, and a rotatable rotating arm or a moving trajectory device equipped with the detection unit may be connected to the detection unit. The X-ray detection unit may perform X-ray imaging at each different position while moving along the rotating arm or the moving trajectory device from the outer side of the oral cavity. The images thus captured may be treated by a computer to be combined with each other as one completed panoramic image. The present exemplary embodiment has advantages in that it is possible to obtain a panoramic image with at least three times shooting and to use general dental equipment.

FIGS. 1 to 3 illustrate, as the X-ray imaging system, the X-ray generating unit 100, the X-ray detection unit 200, and the X-ray generating unit support 330 supporting the unit. The X-ray generating unit 100 is configured to receive a high voltage from the outside through the X-ray generating unit support 330 and is connected to a high voltage power supply through the power supply connection line 331 inside the support if possible.

In order to control the X-ray generating unit support 330 by using a controller from the outside, it is possible to directly control the X-ray generating unit support 330 by adding a motor which may control the position at the joint site, or to remotely manipulate the X-ray generating unit support 330 through a wire connection to a driving shaft.

The X-ray generating unit 100 in FIG. 4 includes an X-ray tube 110 and an X-ray generator 120 with the X-ray tube 110 inserted therein. At this time, the X-ray generator 120 has a collimator 121 provided with an insertion space into which the X-ray tube 110 is introduced and a characteristic that an X-ray emitted from the X-ray tube 110 is radiated in a direction of 360° based on the axis of the X-ray tube at one cross-section of the X-ray tube. It is necessary to limit the radiation radiated from the tube so as to correspond to the range of an object to be photographed. In order to photograph a region of a plurality of teeth, a collimator with a wide opening is installed to control the radiation of the X-ray. A collimator hole 122 is provided in a distal end region of an upper side of the collimator 121. The collimator hole may control both the lateral region and vertical region of the radiation, and thus the collimator is usually configured as one body or may be configured to be separable. In addition, it is possible to hold a rotation device which is rotated by the external control. When a rotatable collimator is used, an X-ray image may be photographed by rotating the position of the opening of the collimator in connection with the position movement of the external X-ray detector. When a rotating collimator is used, it is disadvantageous that the number of devices is slightly increased, but advantageous that the dose of radiation exposed to a patient may be minimized. As described in the above-described exemplary embodiments, when a fixed-type collimator is used, the same effects may be obtained by adding a rotation device to the X-ray generating unit support.

Moreover, an aluminum filter 123 is provided inside the collimator hole 122. Here, the X-ray generated from the X-ray tube 110 is radiated only to a region of the collimator hole 122 of the X-ray generator 120. With this configuration, even though the X-ray tube 110 is inserted into the oral cavity, it is possible to prevent radiation exposure caused by irradiation of X-ray on a region other than the imaging region (that is, a region in which images are obtained).

In the case of the X-ray for imaging the oral cavity, a relatively weak X-ray is used, compared to the usual maximum tube voltage of 200 kVp for treatment purpose. The energy required for the X-ray imaging of the oral cavity is 50 to 100 kVp in terms of tube voltage. Considering the visibility of the image photographed and the like while minimizing the dose of radiation exposed to a patient, it is most preferred that the maximum tube voltage of an appropriate X-ray energy is 60 to 70 kVp, the tube current is 1 to 15 mA, and the exposure time is in a range from 0.02 to 2 seconds.

The X-ray generating unit 100 in the present exemplary embodiment is an apparatus using a field electron emission-based X-ray tube or thermoelectronic emission-based X-ray tube of a nano-composite material and is manufactured to be small-sized so as to be placed in the oral cavity. Furthermore, the X-ray tube includes an electron emitting source which emits electrons and an X-ray emitting unit which emits X-ray excited by electrons emitted, and at this time, when the movement of electrons emitted from the electron emitting source is elongated, the visibility of an image during the X-ray imaging deteriorates, and thus it is preferred that the length is be limited to a region of 3 cm or less. As the electron emitting source, carbon nanotubes (CNT) or filaments may be used.

As shown in FIG. 4, the X-ray generating unit 100 is manufactured in the form of tube, and it is effective to manufacture a tube having a diameter of 10 mm or less (about 0.5 to 10 mm) and a length of 4 cm or less (about 0.5 to 4 cm). At this time, when the diameter is larger than the above-described range, it is disadvantageous that it is difficult to insert the tube into the oral cavity of a patient, and when the length is larger than the above-described range, it is disadvantageous that it is difficult to effectively irradiate the X-ray on an affected area. The X-ray detection unit 200 detects X-ray irradiated from the X-ray generating unit 100. In the present exemplary embodiment, as the X-ray detection unit 200, sensors are used which are sensitive to the X-ray radiation, such as a CMOS, a CCD, a non-pixel-based sensor, an amorphous silicon sensor, or a GEM detector. Furthermore, an image may be obtained even when an X-ray film in the related art is used. When an X-ray sensor is used as the X-ray detection unit 200, it is advantageous that it is easy to process a digital image obtained and it is possible to directly confirm the image on a monitor. Further, it is advantageous that images photographed at various angles may also be processed to form a three-dimensional image, and thus many pieces of X-ray imaging equipment have recently utilized an X-ray sensor.

FIG. 5 is a view illustrating an X-ray generating unit, an X-ray generating unit support, an X-ray detection unit, and a rotation arm which rotates an X-ray detection unit to correspond to imaging positions, in X-ray imaging equipment. The X-ray detection unit 200 obtains necessary images while being rotated by a rotation arm 310 on the outer side of the oral cavity of a patient during the continuous imaging. At this time, the X-ray generating unit 100 is maintained while being fixed at one position by an X-ray generating unit support 320, and emits X-rays while being fixed after the position movement of the X-ray detection unit 200.

FIG. 6 illustrates a cross-section of the X-ray generating unit support 320. The radiation tube of the present invention has an advantage in that a wide region of teeth and the jaw bone may be simultaneously measured due to characteristics of the radiation being radiated at 360° from the end thereof. Further, it is also possible to photograph the upper jaw and the lower jaw simultaneously, and thus a desired image may be obtained with a fewer number of shootings, thereby minimizing the dose of radiation exposed to a patient.

Considering the safety of the X-ray generating unit, the X-ray generating unit uses high voltage and some portions of the X-ray generating unit support are also placed in the oral cavity, and thus it is necessary to use an insulator 332 having excellent insulation characteristics to doubly insulate a high voltage line treated with a primary insulation treatment such that the insulation breakdown does not occur at a high voltage due to moisture in consideration of the safety of a patient. An insulation material different from the insulation material used in the covering of a high voltage line is used to have insulation characteristics. The X-ray generating unit may also be manufactured by using glass fiber. It is also possible to configure a stacked form of an insulating material and a non-insulating material. Here, in additionally describing the non-insulating material, the non-insulator means installing a conductor using a ground electric potential in the X-ray generating unit 100 or the X-ray generating unit support 330. A ground electric potential conductor 333 may be subjected to a conductor coating, and may also be surrounded by an instrument material using a separate conducting material. The most preferred configuration is to surround an insulating material vulnerable to moisture with a metal material to conduct a water-proofing treatment. In addition, electromagnetic effects of a high voltage power supply on the peripheral devices are reduced by blocking the high voltage power supply with a conductor of ground electric potential, thereby improving the electrical operation stability performance.

An imaging method of an X-ray image using an X-ray imaging system having the above-described configuration will be described.

Referring to FIG. 1, the X-ray generating unit 100 is disposed in an imaging region in the oral cavity of a patient. Subsequently, the X-ray detection unit 200 is disposed on the outer side of the oral cavity of a patient, which corresponds to the X-ray generating unit 100. Subsequently, a radiation direction of an X-ray and a sensor direction of the X-ray detection unit 200 are arranged through the collimator. When the arrangement is completed, a high voltage is applied to the X-ray generating unit 100 to emit an X-ray in the oral cavity. At this time, the X-ray emitted is received as digital data through a sensor of the X-ray detection unit 200 to form an image.

The imaging method of an X-ray image in another exemplary embodiment is as follows.

Referring to FIG. 2, the X-ray generating unit 100 is disposed in an imaging region in the oral cavity of a patient. Subsequently, the X-ray detection unit 200 is disposed on the outer side of the oral cavity of a patient, which corresponds to the X-ray generating unit 100. A high voltage is applied to the X-ray generating unit 100 to emit an X-ray in the oral cavity. At this time, the X-ray emitted is received as digital data through a sensor of the X-ray detection unit 200 to form an image. The position of the X-ray detection unit is transferred to the position of the next X-ray imaging by a rotation arm or a moving trajectory device. A high voltage is applied to the X-ray generating unit 100 to emit an X-ray in the oral cavity. At this time, the X-ray emitted is received as digital data through a sensor of the X-ray detection unit 200 to form an image. A plurality of images is obtained, and then one X-ray image is generated through a computer image processing.

The invention claimed is:

1. An intraoral radiation type X-ray imaging system for capturing an X-ray image of teeth or a jawbone, comprising:
    an X-ray generating unit to be placed in an oral cavity; and
    an X-ray detection unit corresponding to the X-ray generating unit and to be placed on the outer side of the oral cavity,
    wherein the X-ray generating unit comprises:
    a tubular electron emitting source and X-ray emitting source, the electron emitting source supplying electrons to the X-ray emitting source, and
    a collimator,
    wherein the X-ray emitting source emits X-rays at 360° and the collimator regulates the radiation direction of the emitted X-rays to an angle less than 360°.

2. The intraoral radiation type X-ray imaging system as claimed in claim 1, wherein the collimator regulates the radiation dose of the X-ray generated.

3. The intraoral radiation type X-ray imaging system as claimed in claim 1, wherein a distance between the electron emitting source and the X-ray emitting source of the X-ray generating unit is 3 cm or less.

4. The intraoral radiation type X-ray imaging system as claimed in claim 1, wherein in the X-ray generating unit, a field electron emission-based X-ray tube or thermoelectronic emission-based X-ray tube of a nano-composite material is used.

5. The intraoral radiation type X-ray imaging system as claimed in claim 1, wherein a maximum tube voltage applied to the X-ray generating unit is 60 to 70 kVp and a tube current is 1 to 15 mA.

6. The intraoral radiation type X-ray imaging system as claimed in claim 5, wherein an electric power applied for generating X-ray to the X-ray generating unit is supplied for 0.02 to 2 seconds per round.

7. The intraoral radiation type X-ray imaging system as claimed in claim 1, wherein the X-ray detection unit uses any one of a CMOS, a CCD, a non-pixel-based sensor, an amorphous silicon sensor and a GEM detector.

8. The intraoral radiation type X-ray imaging system as claimed in claim 1, wherein one side of the X-ray generating unit is connected to an X-ray generating unit support having flexibility.

9. The intraoral radiation type X-ray imaging system as claimed in claim 8, wherein the X-ray generating unit support comprises joints or is made of an elastic material.

10. The intraoral radiation type X-ray imaging system as claimed in claim 8, wherein the X-ray generating unit support comprises an X-ray generating unit power supply line therein.

11. The intraoral radiation type X-ray imaging system as claimed in claim 10, wherein the X-ray generating unit power supply line of the X-ray generating unit support comprises an insulator insulated with two or more insulating materials on the outer side of the line.

12. The intraoral radiation type X-ray imaging system as claimed in claim 10, wherein the X-ray generating unit support comprises a ground conductor placed on the outer side of the X-ray generating unit power supply line.

13. The intraoral radiation type X-ray imaging system as claimed in claim 10, wherein the X-ray generating unit support comprises an insulator that insulates the outer side of the X-ray generating unit power supply line with two or more insulating materials and a ground conductor.

14. The intraoral radiation type X-ray imaging system as claimed in claim 1, further comprising:
    an X-ray detection unit transferring means connected to the X-ray detection unit and to be moved along the outer side of the oral cavity of a patient.

15. The intraoral radiation type X-ray imaging system as claimed in claim 14, wherein the X-ray detection unit transferring means is any one of a rotation arm that rotates about the X-ray generating source, and a previously disposed trajectory device.

16. The intraoral radiation type X-ray imaging system as claimed in claim 14, wherein the X-ray generating unit is connected at one side to an X-ray generating unit support comprising joints or formed of a flexible material and is fixed during the position movement of the X-ray detection unit.

17. An intraoral radiation type X-ray imaging system for capturing an X-ray image of teeth or a jawbone, comprising:
    an X-ray generating unit placed in an oral cavity; and
    an X-ray detection unit corresponding to the X-ray generating unit and disposed in a continuous curve on the outer side of an oral cavity of a patient such that the entire X-ray image of at least one of the upper jaw and lower jaw is obtained simultaneously with one time of X-ray generation.

18. The intraoral radiation type X-ray imaging system as claimed in claim 17, wherein an electric power with a voltage of 50 to 100 kVp and a current of 1 to 15 mA is applied for 0.02 to 2 seconds to the X-ray emitting source provided in the X-ray generating unit through an X-ray generating unit power source line placed in the oral cavity such that the electric power is supplied to the X-ray generating unit.

19. An intraoral radiation type method for capturing an intraoral X-ray image through an X-ray imaging system comprising an X-ray generating unit, an X-ray detection unit, and an arm unit for transferring the X-ray generating unit and the X-ray detection unit, the method including:
- operating an X-ray emitting source of the X-ray generating unit to emit X-rays at 360° and collimating the emitted X-rays so as to regulate the radiation direction of the emitted X-rays to an angle less than 360°;
- transferring the arm unit to dispose the X-ray generating unit at an imaging region of the oral cavity of a patient or inside a human body;
- disposing the X-ray detection unit at the outer side of the oral cavity or the human body;
- arranging the X-ray emitting direction of the X-ray generating unit and the X-ray detection unit placed on the outer side of the oral cavity or the human body to correspond to each other; and
- applying voltage for generating the X-ray to the X-ray generating unit to obtain the X-ray image.

20. The method as claimed in claim 19, wherein the X-ray detection unit is disposed in a continuous curve on the outer side of the oral cavity such that the entire X-ray image of at least one of the upper jaw and lower jaw is obtained simultaneously with one time of X-ray generation.

* * * * *